(12) United States Patent
Stauffer

(10) Patent No.: US 10,040,737 B2
(45) Date of Patent: Aug. 7, 2018

(54) METHANOL PRODUCTION FROM METHANE AND CARBON DIOXIDE

(71) Applicant: John E. Stauffer, Greenwich, CT (US)

(72) Inventor: John E. Stauffer, Greenwich, CT (US)

( * ) Notice: Subject to any disclaimer, the term of this patent is extended or adjusted under 35 U.S.C. 154(b) by 216 days.

(21) Appl. No.: 14/798,898

(22) Filed: Jul. 14, 2015

(65) Prior Publication Data
US 2017/0015611 A1 Jan. 19, 2017

(51) Int. Cl.
| | | |
|---|---|---|
| *C07C 29/48* | (2006.01) | |
| *C07C 29/159* | (2006.01) | |
| *C07C 29/74* | (2006.01) | |
| *F02C 6/00* | (2006.01) | |

(52) U.S. Cl.
CPC ............ *C07C 29/48* (2013.01); *C07C 29/159* (2013.01); *C07C 29/74* (2013.01); *F02C 6/00* (2013.01); *F05D 2260/61* (2013.01); *Y02P 20/142* (2015.11)

(58) Field of Classification Search
CPC combination set(s) only.
See application file for complete search history.

(56) References Cited

U.S. PATENT DOCUMENTS

| | | | |
|---|---|---|---|
| 1,849,844 A | 3/1932 | Joseph et al. | |
| 2,276,192 A | 3/1942 | Hanford et al. | |
| 3,497,436 A | 2/1970 | Burleson et al. | |
| 4,364,915 A | 12/1982 | Proctor | |
| 4,562,174 A | 12/1985 | Stiles | |
| 4,825,004 A | 4/1989 | Rutzen et al. | |
| 4,913,842 A | 4/1990 | Yoneoka et al. | |
| 5,070,016 A | 12/1991 | Hallberg | |
| 5,395,991 A | 3/1995 | Scarlett et al. | |
| 5,449,696 A | 9/1995 | Dandekar et al. | |
| 5,453,412 A | 9/1995 | Deckers et al. | |
| 5,663,429 A | 9/1997 | Yamaseki et al. | |
| 6,114,279 A | 9/2000 | Fukui et al. | |
| 6,140,545 A | 10/2000 | Merger et al. | |
| 6,274,108 B1 | 8/2001 | Fujii et al. | |
| 6,452,058 B1 | 9/2002 | Schweizer et al. | |
| 6,486,368 B1 | 11/2002 | Zhou et al. | |
| 6,632,330 B1 | 10/2003 | Colley et al. | |
| 7,199,276 B2 | 4/2007 | Sher et al. | |
| 7,214,721 B2 | 5/2007 | Eastland | |
| 7,288,689 B2 | 10/2007 | Janssen et al. | |
| 7,696,390 B2 | 4/2010 | Stauffer | |
| 7,906,559 B2 * | 3/2011 | Olah | C01B 3/38 518/704 |
| 7,977,272 B2 | 7/2011 | Miller et al. | |
| 8,323,602 B2 | 12/2012 | Wright et al. | |
| 8,440,868 B2 | 5/2013 | Stauffer | |
| 8,512,460 B2 | 8/2013 | Moniwa et al. | |
| 8,581,010 B2 | 11/2013 | Stauffer | |
| 8,728,423 B2 | 5/2014 | Iijima et al. | |
| 8,795,415 B2 | 8/2014 | Katz et al. | |
| 8,961,664 B2 | 2/2015 | Nakayama et al. | |
| 9,155,991 B2 | 10/2015 | Ogawa et al. | |
| 2007/0282018 A1 | 12/2007 | Jenkins et al. | |
| 2008/0269519 A1 | 10/2008 | Miller et al. | |
| 2010/0261125 A1 | 10/2010 | Olah et al. | |
| 2012/0259145 A1 | 10/2012 | Stauffer | |

FOREIGN PATENT DOCUMENTS

| | | |
|---|---|---|
| DE | 362746 C | 10/1922 |
| WO | WO2008080767 A1 | 7/2008 |
| WO | WO2014/096226 * | 6/2014 |

OTHER PUBLICATIONS

European Search Report, EP 09 25 1524, dated Sep. 1, 2009.
International Search Report, PCT/EP2007/063570, dated Dec. 3, 2008.
V.N. Ipatieff, G. S. Monroe: "Synthesis of Methanol from Carbon Dioxide and Hydrogen over Copper-Alumina Catalysts. Mechanism of Reaction" J. AM. Chem. Soc., vol. 67, No. 12, Dec. 1945 (Dec. 1945), pp. 2168-2171, SP002543626.

\* cited by examiner

*Primary Examiner* — Pancham Bakshi
*Assistant Examiner* — Mark R Luderer
(74) *Attorney, Agent, or Firm* — Young Basile Hanlon & MacFarlane, P.C.

(57) ABSTRACT

Carbon dioxide is reacted with methane in a free radical reaction to produce methanol and carbon monoxide. A system for producing carbon dioxide as a feed ingredient for the process through electric power generator is disclosed.

4 Claims, 2 Drawing Sheets

METHANOL PRODUCTION FROM METHANE AND CARBON DIOXIDE

FIELD OF THE INVENTION

Existing technology relates to a process for the production of methanol wherein carbon dioxide is reacted with methane.

BACKGROUND

Existing technology is capable of producing methanol from methane and carbon dioxide, however it is a long, tedious and expensive undertaking. Multiple reactions are required for which dedicated equipment is needed. Like many organic preparations, conversions are low and repeated separations are involved. At the heart of the process is the generation of synthesis gas with all that such chemistry implies: high pressure, elevated temperatures and finicky catalysts.

To illustrate the known procedures for producing methanol, the following equations are helpful.

$$CO_2 + 3\ H_2 \rightarrow CH_3OH + H_2O \qquad 1.$$

$$CH_4 + H_2O \rightarrow CO + 3\ H_2 \qquad 2.$$

Equation no. 1 represents the classical reaction for producing methanol from synthesis gas. The reaction requires moderate temperature, high pressure and a catalyst based on a copper-zinc compound.

Equation no. 2 shows the formation of synthesis gas by methane steam reforming. High temperatures are required as well as a catalyst typically comprising nickel.

When equations 1 and 2 are combined, the following relationship is obtained.

$$CH_4 + CO_2 \rightarrow CH_3OH + CO \qquad 3.$$

The expression represents the goal of the exercise, namely, the production of methanol from methane and carbon dioxide. Nevertheless, the procedure is indirect and necessitates substantial investment.

Because widespread recovery of carbon dioxide is not practiced, a source of oxygen is required for current operations. Thus, air separation units are needed to provide oxygen to existing methanol facilities. This requirement presents an added cost.

As priorities begin to shift toward more environmentally friendly practices, carbon dioxide will likely assume greater attention. Its recovery and disposition may become mandatory. With this trend in mind, there is an incentive to develop improved technology for the production of methanol using carbon dioxide as a feedstock. This and other objectives of the present invention will become apparent from the discussion that follows and the illustration therewith.

DETAILED DESCRIPTION

Figure 1:
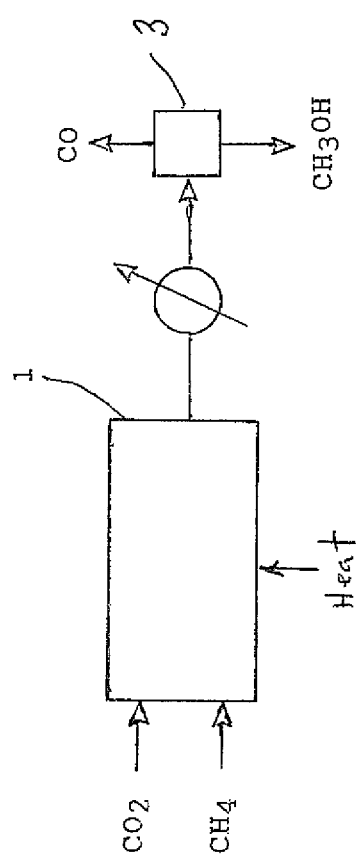
FIG. 1 is a rendering of the process indicating the feed streams to a reactor and the product produced.

The present invention takes advantage of two factors: first, the perceived urgency to recover and sequester large quantities of carbon dioxide to mitigate the effects of global warming; second, the availability of new supplies of cheap natural gas from fracking, take advantage of these two factors by reacting. carbon dioxide with methane gas to make methanol.

The chemistry works in favor of a useful product. The free radical reactions that take place by combining methane with carbon dioxide are shown as follows.

$$CH_4 \rightarrow CH_3\cdot + H\cdot \qquad 4.$$

$$CH_4 + OH\cdot \rightarrow CH_3OH + H\cdot \qquad 5.$$

$$CO_2 + H\cdot \rightarrow CO + OH\cdot \qquad 6.$$

$$CH_3\cdot + OH\cdot \rightarrow CH_3OH \qquad 7.$$

In the above series of equations, equation no. 4 represents the initiation reaction. Equation nos. 5 and 6 represent the chain reactions. And equation no. 7 is the terminal reaction.

As in any free radical phenomena, the overall reaction is extremely fast because the chain reactions occur with lightning speed. No catalyst is required under these conditions.

When equation nos. 5 and 6 are combined, the net result is the following.

$$CH_4 + CO_2 \rightarrow CH_3OH + CO \qquad 8.$$

This is the same outcome as can be obtained by existing technology (equation no. 3), except that the present invention achieves the result in a one-step process that proceeds with high efficiency.

In the free radical reactions that take place, the radicals H· and OH· are the same ones that occur in the combustion of fuels. The methanol product is relatively stable as suggested by the process for formaldehyde, which requires a catalyst at 600° to 650° C. to decompose methanol. Finally, carbon monoxide can be thought of as a sink in the reaction mechanism. The bond dissociation energy for C—O is 1076.5 kJ/mol, exceeding by far other bond energies.

The conditions for the free radical reaction of the present invention are critical. Near atmospheric pressure is assumed. This mirrors combustion reactions. The temperatures of the reaction must be sufficiently high to sever the chemical bonds. From experience, the temperature is in the range of 600° to 1000° C. The holding time at this temperature is extremely short, thus requiring a flow reactor design.

The simplicity of the present invention is illustrated by FIG. 1. Reactor 1, for example, comprises a coil of hollow tubing through which the reactants flow. This coil is heated in a furnace. The exit gases are quenched and product is separated at 3 from carbon monoxide.

Figure 2:
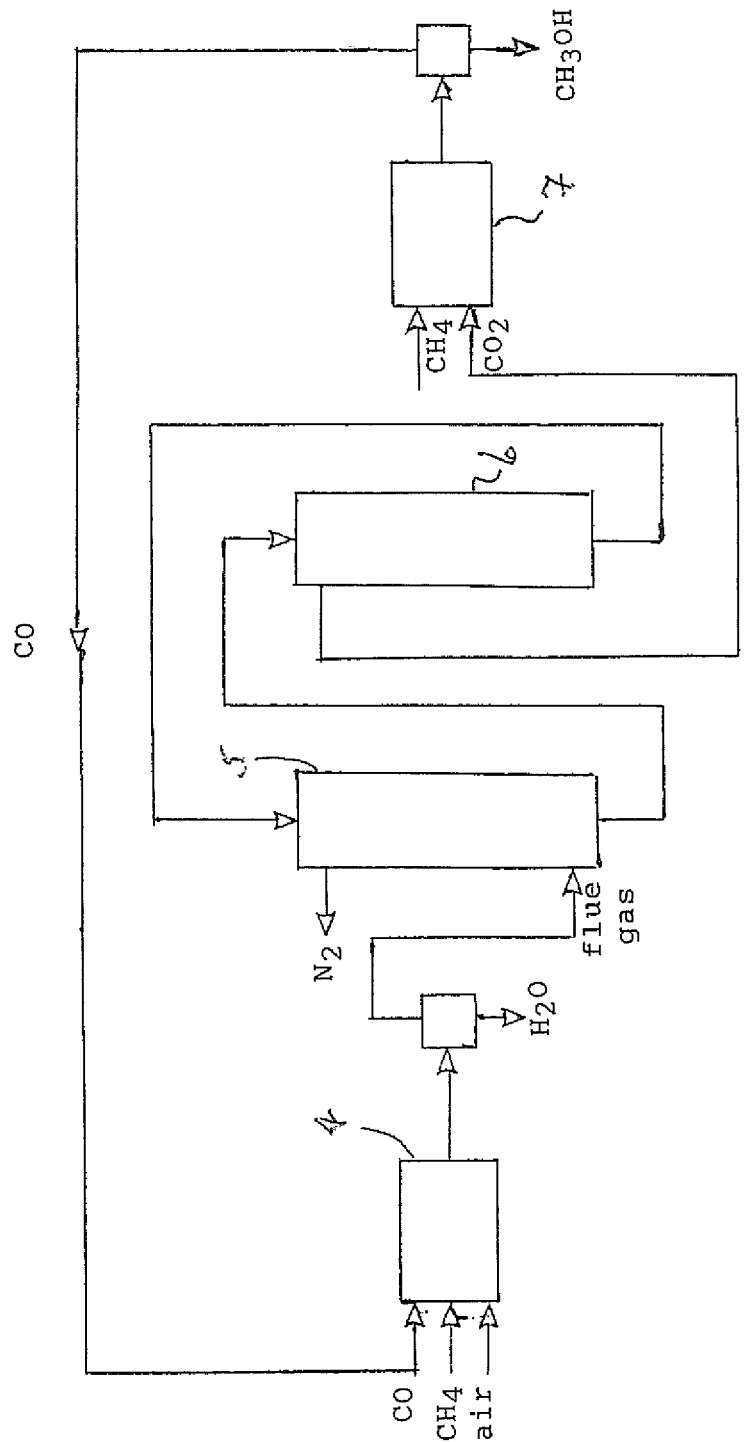
FIG. 2 shows a practical application of the present invention in the production of electric power.

An application of the present invention is shown in FIG. 2 for electric power generation. Turbine 4 is driven by combustion gases. Absorption Column 5 and Stripping Column 6 recover carbon dioxide from the flue gas. Methane and carbon dioxide produce methanol and carbon monoxide in Reactor 7. The separate units are integrated so that the only product is methanol.

SUMMARY

Methyl alcohol or methanol is produced from methane and carbon dioxide in a free radical reaction. In the process, the two reactants are mixed and heated to a high temperature and rapidly quenched, thereby producing methanol and carbon monoxide. The methanol is separated and purified from any byproducts by, for example, distillation.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A process for the production of methanol and carbon monoxide from methane and carbon dioxde in a single step using a flow reactor and comprising a non-catalytic free radical reaction involving $CH_3\bullet$ and $H\bullet$, $\emptyset H\bullet$ as reactive free radicals conducted at about one atmosphere pressure and at a temperature in the range of 600° C. to 1000° C.

2. A process for the production of methanol comprising the steps of:
   a. mixing carbon dioxide with methane at a temperature of between about 600° C. and 1000° C. using a flow reactor and in the absence of a catalyst in a free radical reaction to produce methanol and carbon monoxide; and
   b. separating the carbon monoxide from the methanol.

3. The process of claim 2 wherein the reactants carbon dioxide and methane are quenched after high temperature mixing.

4. A process for the production of electric powers comprising the steps of:
   a. driving a turbine by combustion gas to produce flue gases;
   b. recovering carbon dioxide from flue gases produced in step (a); and
   c. using the carbon dioxide in the process of claim 3 to produce methanol.

* * * * *